US012721740B2

(12) United States Patent
Mönicke et al.

(10) Patent No.: US 12,721,740 B2
(45) Date of Patent: Sep. 1, 2026

(54) PROSTHETIC FOOT

(71) Applicant: OTTOBOCK SE & CO. KGAA, Duderstadt (DE)

(72) Inventors: Carsten Mönicke, Duderstadt (DE); Hermann Meyer, Duderstadt (DE); Martin Karstens, Duderstadt (DE); Hannes Krenz, Duderstadt (DE); Tobias Ott, Duderstadt (DE); Sven Kubitz, Duderstadt (DE); Miclas Schwartz, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 714 days.

(21) Appl. No.: 18/040,347

(22) PCT Filed: Aug. 3, 2021

(86) PCT No.: PCT/EP2021/071650

§ 371 (c)(1),
(2) Date: Feb. 2, 2023

(87) PCT Pub. No.: WO2022/029114

PCT Pub. Date: Feb. 10, 2022

(65) Prior Publication Data

US 2023/0301804 A1 Sep. 28, 2023

(30) Foreign Application Priority Data

Aug. 4, 2020 (DE) ..................... 10 2020 120 498.1

(51) Int. Cl.

| | |
|---|---|
| ***A61F 2/66*** | (2006.01) |
| *A61F 2/50* | (2006.01) |
| *A61F 2/60* | (2006.01) |
| *A61F 2/68* | (2006.01) |

(52) U.S. Cl.
CPC .... *A61F 2/6607* (2013.01); *A61F 2002/5038* (2013.01); *A61F 2002/5087* (2013.01);
(Continued)

(58) Field of Classification Search
CPC .. A61F 2/6607; A61F 2/74; A61F 2002/5038; A61F 2002/6854
See application file for complete search history.

(56) References Cited

U.S. PATENT DOCUMENTS 5,728,175 A 3/1998 Rincoe
5,888,239 A 3/1999 Wellershaus et al.
(Continued)

FOREIGN PATENT DOCUMENTS

CN 111084682 A 5/2020
DE 102014006228 A1 * 11/2015 ............... A61F 2/66
(Continued)

OTHER PUBLICATIONS

Translation of DE10214006228A (Year: 2015).*
Translation of WO2015165981A1 (Year: 2015).*

*Primary Examiner* — Christie Bahena
(74) *Attorney, Agent, or Firm* — WCF IP

(57) ABSTRACT

The invention relates to a prosthetic foot with
a foot part 2 and
a lower leg part 4 that is connected to the foot part 2 such that it can be pivoted about a pivot axis 6 and that can be locked in various pivot angles relative to the foot part 2,
the connection between the lower leg part 4 and the foot part 2 having a clearance in the pivot direction when the foot part 2 is locked on the lower leg part 4, the prosthetic foot having at least one friction element 14 arranged between the foot part 2 and the lower leg part 4 and applying a frictional torque that counteracts a
(Continued)

Figure 5:
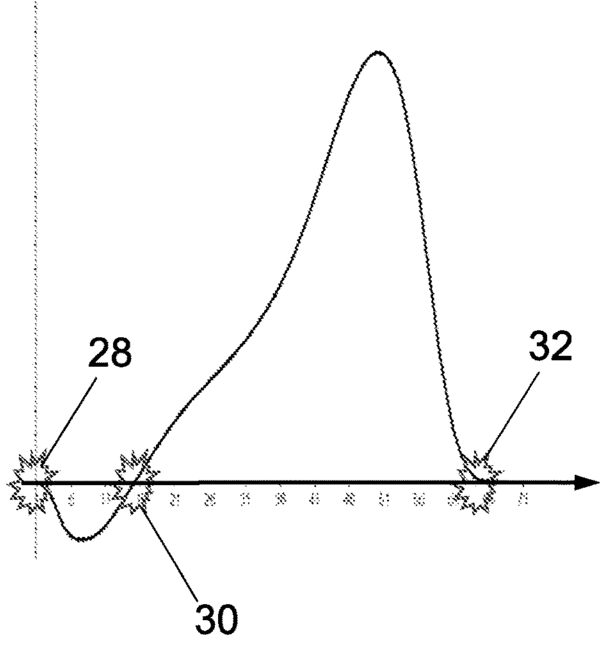

pivoting of the foot part 2 relative to the lower leg part 4 when the foot part 2 is locked relative to the lower leg part 4.

9 Claims, 6 Drawing Sheets

(52) U.S. Cl.
CPC . *A61F 2002/607* (2013.01); *A61F 2002/6664* (2013.01); *A61F 2002/6854* (2013.01)

(56) References Cited

U.S. PATENT DOCUMENTS

| | | | | |
|---|---|---|---|---|
| 5,913,901 | A * | 6/1999 | Lacroix | A61F 2/6607 623/47 |
| 7,416,565 | B1 | 8/2008 | Al-Turaikl | |
| 7,862,622 | B2 | 1/2011 | Dunlap et al. | |
| 8,048,172 | B2 | 11/2011 | Josson et al. | |
| 8,317,875 | B2 | 11/2012 | Josson et al. | |
| 10,034,783 | B1 * | 7/2018 | Highsmith | A61F 2/76 |
| 2005/0085926 | A1 * | 4/2005 | Christensen | A61F 2/6607 623/47 |
| 2007/0156252 | A1 * | 7/2007 | Jonsson | A61F 2/66 623/47 |
| 2017/0128236 | A1 | 5/2017 | Meyer et al. | |

FOREIGN PATENT DOCUMENTS

| | | | | |
|---|---|---|---|---|
| DE | 10 2014 010 938 | A1 | 1/2016 | |
| EP | 3 137 020 | B1 | 1/2018 | |
| WO | WO-2015165981 | A1 * | 11/2015 | A61F 2/66 |

* cited by examiner

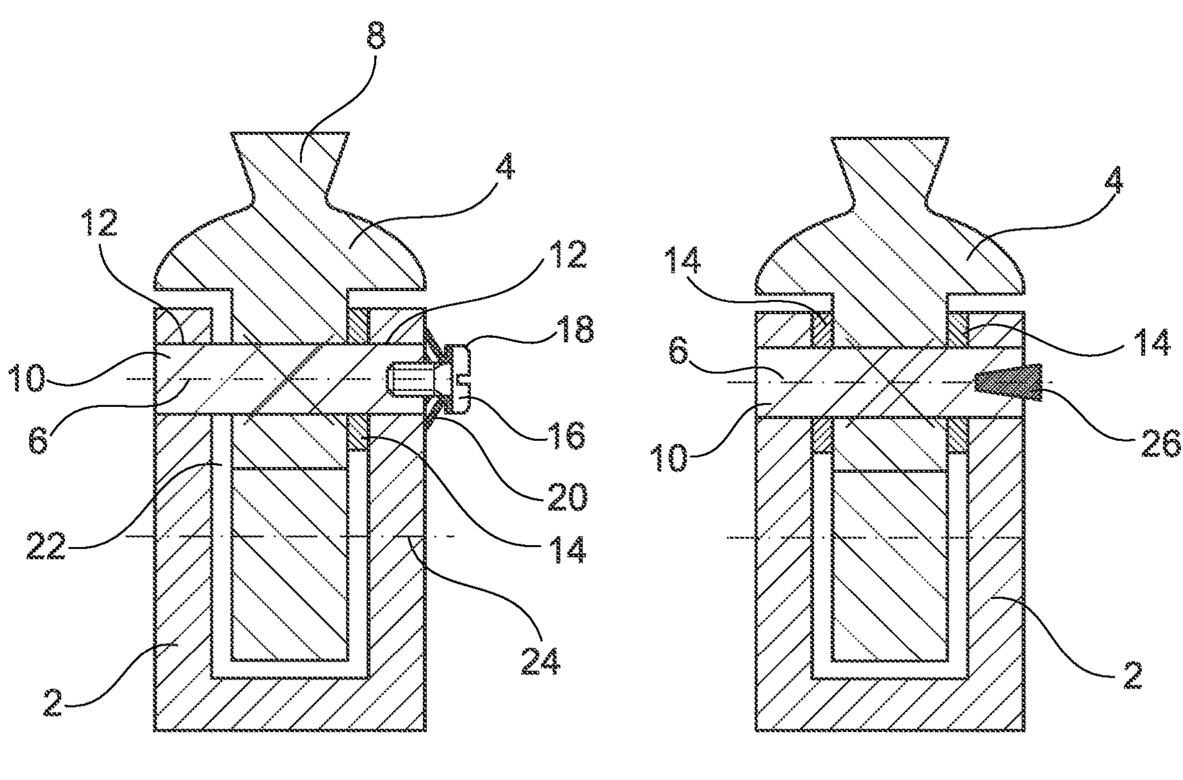
Fig. 1
Fig. 2
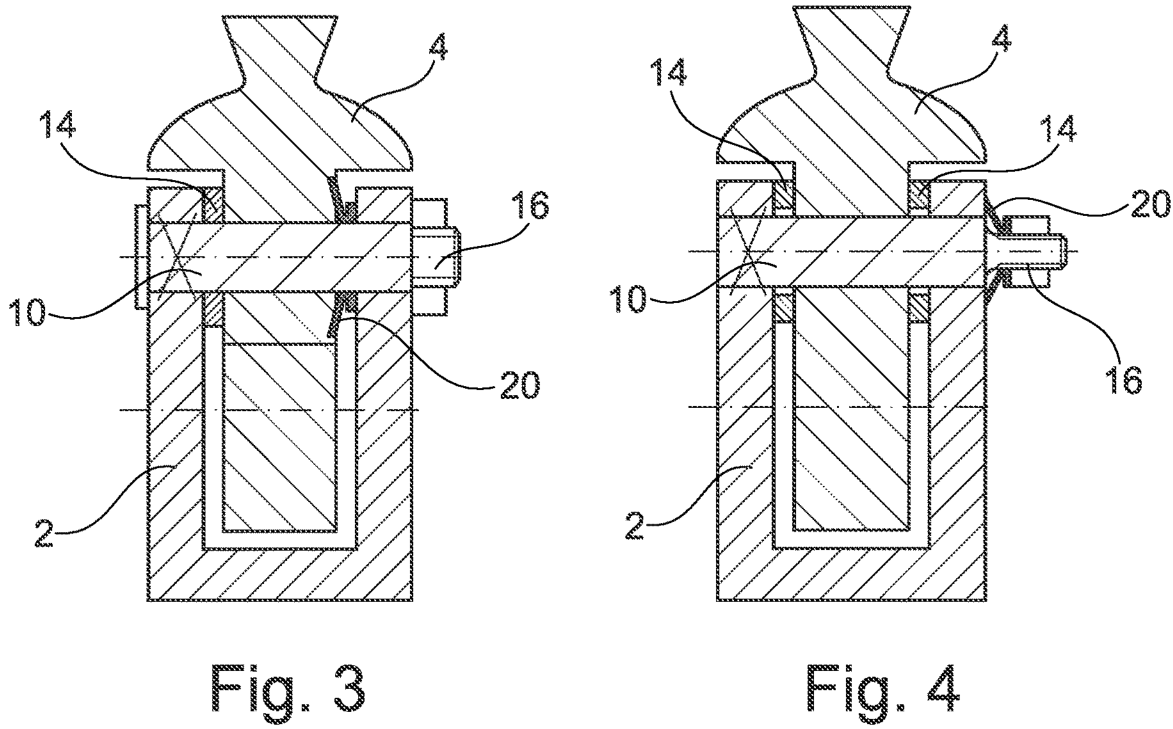
Fig. 3
Fig. 4

PROSTHETIC FOOT

The invention relates to a prosthetic foot with a foot part and a lower leg part, which is connected to the foot part such that it can be pivoted about a pivot axis and locked at various pivot angles relative to the foot part, the connection between the lower leg part and the foot part having a clearance in the pivot direction when the foot part is locked on the lower leg part.

A prosthetic foot according to the preamble is known, for example, from DE 10 2014 010 938 A1. In particular, such prosthetic feet have a heel height adjustment function. The foot part can be locked at various pivot angles relative to the lower leg part. For example, an angle between a sole of a foot, I.e. in particular the contact surface of the prosthetic foot with which the prosthetic foot is to come into contact with the ground, and the lower leg part or a lower leg arranged on the lower leg part can thus be adjusted. This is especially advantageous if the wearer of the prosthetic foot wishes to wear shoes with different sized heels. The higher the heel, the steeper the foot part must be.

Heel height adjustment functions have been known for many years and are well-established in the prior art. Preferably, the corresponding embodiments are designed in such a way that it is as easy as possible to adjust the heel height, so the wearer of the prosthetic foot can quickly carry out a corresponding adjustment without outside help and preferably without tools, for example if the shoe is to be changed.

Various mechanisms are known from the prior art that are used to lock the foot part on the lower leg part at different pivot angles. In an especially simple embodiment, both the lower leg part and the foot part feature multiple bores, which can be brought into overlap with each other in various positions and orientations of the two components. In these positions and orientations, a peg or bolt, for example, is then pushed through the bores so that the two components are locked relative to each other. Due to production tolerances, such connections have a clearance in the pivot direction because the dimensions of the diameter of the peg or bolt are usually smaller than those of the diameter of the bore. The pivot axis, by means of which a heel height can be adjusted, extends at least almost, but in most prosthetic feet from the prior art precisely, from medial to lateral, i.e. transversely to the direction of travel of the prosthetic foot.

During a step, the prosthetic foot is first set down with the heel. This so-called "heel strike" constitutes the beginning of the stance phase of the step, in which the prosthetic foot is in contact with the ground. Loading the prosthetic foot on the heel generates a torque about the pivot axis that acts in the direction of plantar flexion. A plantar flexion refers to the lowering of the toes and the forefoot area. During the stance phase, the load point shifts towards the forefoot of the prosthetic foot (frontally) until the moment at which the toes leave the ground ("toe-off"), which also defines the end of the stance phase. At this moment, the prosthetic foot is only loaded in the forefoot area and a torque develops that acts in the direction of dorsal flexion. The dorsal flexion is the opposite movement to the plantar flexion and describes the raising of the forefoot and the toes in the direction of the lower leg.

Due to the clearance of the connection between foot part and lower leg part, the foot part can be minimally pivoted relative to the lower leg part when the two components are locked relative to each other. At the beginning of a stance phase, the foot part is thus pivoted relative to the lower leg part in the plantar flexion direction until it strikes. Over the course of the step, the torque changes sign and the foot part is pivoted relative to the lower leg part in the dorsal flexion direction until it strikes. There are consequently two hard impacts in a single step that create an audible noise. This is considered a disadvantage because, for example, it betrays the prosthesis wearer as such.

The prior art therefore suggests various methods for preventing these movements due to the clearance. For example, U.S. Pat. No. 8,317,875 B2 discloses a prosthetic foot according to the preamble in which the lower leg part is pressurized with a spring-loaded pin, which exerts a force so great that the loads that occur when walking are not enough to bring about a relative movement between foot part and lower leg part. U.S. Pat. No. 7,416,565 B1, on the other hand, discloses a fastening between foot part and lower leg part that prevents clearance by means of a wrap spring.

The disadvantage of these solutions is that the respective designs make it more difficult to release a locking between the foot part and the lower leg part. The same applies, for example, for embodiments in which a screw, rather than a peg or a bolt, is guided through the bores described above and the foot part and the lower leg part are braced against each other by means of a nut in such a way that movement caused by clearance is prevented. In this case too, the release of the lock is more difficult as the bracing must be released first. This is impossible or at least very difficult without tools and possibly outside help.

The invention is therefore based on the task of improving a prosthetic foot in such a way that the foot part can be easily released and relocked in a different position and/or orientation relative to the lower leg part, and with which the disadvantages of the prior art are eliminated or at least reduced.

The invention solves the task addressed by way of a prosthetic foot according to the preamble of claim 1, characterized in that the prosthetic foot comprises at least one friction element, which is arranged between the foot part and the lower leg part and applies a frictional torque that counteracts a pivoting of the foot part relative to the lower leg part when the foot part is locked relative to the lower leg part.

As a result of the embodiment of the prosthetic foot according to the invention, a frictional torque is applied as soon as pivoting enabled by the clearance in the connection between the foot part and the lower leg part occurs. In other words, this frictional torque is always applied when the foot part is pivoted relative to the lower leg part when the two components are locked relative to each other. This movement is only possible due to the existing clearance and is also limited in its scope by the clearance. Due to this frictional torque, the movement is not completely prevented. Rather, it is slowed down, so that the impact of the two components against each other, which also occurs in the embodiment of the prosthetic foot according to the invention, is mitigated. This means that, compared to the prior art, the two components move towards each other more slowly when it comes to the impact. The noise that occurs in prosthetic feet is prevented by the embodiment according to the invention or is at least reduced to such an extent that it is no longer disruptive or, preferably, is not perceived at all. The invention therefore relates in particular to a use of a friction element in a prosthetic foot of the type described above in order to apply a frictional torque that counteracts a pivoting of the foot part relative to the lower leg part when the foot part is locked relative to the lower leg part. The invention is consequently advantageous when the connection between the foot part and the lower leg part has an additional clearance, for example along the pivot axis. This additional clearance can be, but does not have to be, influenced or even offset by the friction element.

Preferably, the frictional torque is constant, irrespective of the position in which the foot part and the lower part are locked in relation to each other and/or independently of the pivot direction in which the movement enabled by the clearance occurs. In particular, the present invention is not concerned with making a step cycle appear more natural by applying damping in one or the other pivot direction. The frictional torque applied is only intended to not fully suppress or render impossible the movement that is possible due to the clearance and therefore actually undesirable, but to slow down this actually undesirable movement so that undesirable noises do not occur or are at least attenuated in their volume.

The pivoting of the foot part relative to the lower leg part made possible by the clearance is preferably smaller than 1°, preferably smaller than 0.5°, especially preferably smaller than 0.25°.

The frictional torque is applied by the at least one friction element arranged between the foot part and the lower leg part. Here, the arrangement "between" the two components means specifically that a movement of the one of the two components relative to the other of the two components generates the frictional torque. It not necessary, but indeed advantageous, for the at least one friction element to be located geometrically between the foot part and the lower leg part. In this case, it is preferably sufficient if a part of the at least one friction element, especially preferably the part that generates the frictional torque, is arranged geometrically between the foot part and the lower leg part. Preferably, the foot part is located entirely on one side of the at least one friction element and the lower leg part entirely on the opposite side of the at least one friction element. However, it is sufficient if a part of the foot part is located on one side of the at least one friction element and a part of the lower leg part is located on the opposite side.

With the embodiment according to the invention, it is also possible to separate the locking device functionally and/or objectively from the friction element. The friction element is preferably independent of the type of locking device, i.e. especially an element or component that plays no role in the locking device. To adjust the foot part relative to the lower leg part, i.e. to lock it at a different pivot angle, it is preferably not necessary to handle, in particular to release or remove, the at least one friction element. Preferably, the at least one friction element also applies the frictional torque when the foot part is moved, particularly pivoted, relative to the lower leg part when the foot part is not locked relative to the lower leg part. In this state, the freedom of movement of the two components is not limited by the clearance.

The friction element is preferably configured to generate the frictional torque independently of whether the foot part is locked relative to the lower leg part, so that the lower part also has to be pivoted relative to the foot part against the frictional torque in this state. The frictional torque is preferably small, for example smaller than 5 Nm, preferably smaller than 2.5 Nm, especially preferably smaller than 2.0 Nm, and greater than 0.5 Nm, preferably greater than 1.0 Nm and especially preferably greater than 1.5 Nm. Such a frictional torque is also easily overcome by the wearer of the prosthetic foot when adjusting the pivot angle at which the foot part is locked relative to the lower leg part.

Preferably, the lower leg part can be locked relative to the foot part by way of a form-fitting connection. In this case, the lower leg part and the foot part preferably have correspondingly designed form-fitting elements. Particularly preferably, the at least one frictional element is arranged on at least one of these form-fitting elements. Here, the at least one friction element is preferably arranged on the form-fitting element in such a way that, when the two components are in the locked state, it comes into contact with the respective other form-fitting element and/or the respective other component and generates the frictional torque due to mechanical friction.

Alternatively or additionally, the lower leg part and the foot part feature form-fitting elements that are designed to correspond to a separate form-fitting component, wherein the at least one friction element is arranged on the form-fitting component and/or on at least one of the form-fitting elements. Particularly preferably, the at least one friction element is arranged on all form-fitting elements. For this purpose, it is advantageous if the at least one friction element is designed in multiple parts and/or the prosthetic foot has multiple friction elements, of which at least one is preferably arranged on each of the form-fitting elements. The form-fitting elements are, for example, bores arranged in the foot part and the lower leg part. The bores can be designed as through bores or blind bores. The bores are brought into overlap at the angles at which the foot part is to be locked on the lower leg part. The form-fitting component, for example in the form of a pin, a bolt, a peg, a screw or a bar, is then inserted into the overlapping bores and secured, where applicable, with a securing element, such as a screw.

Particularly preferably, the form-fitting element is designed in such a way that it can be disengaged manually or mechatronically. In the disengaged position, the heel height can be adjusted. The reset into the locking position can be conducted either manually, mechanically—e.g. via a spring element- or mechatronically. During disengagement, the form-fitting element is displaced along a displacement direction and thus disengaged from the corresponding form-fitting element. When engaging or resetting, the form-fitting element is displaced in the opposite direction and thus re-engaged with the corresponding form-fitting element. The form-fitting element to be displaced is preferably designed as a gearwheel and the displacement direction extends along the axis of rotation of the gearwheel.

The form-fitting component can preferably be mounted on the lower leg part or the foot part. In this case, the form-fitting component which is, for example, inserted into the bores described is preferably connected to the foot part or the lower leg part such that is it torque-proof, so that it can be pivoted with the respective part on which it is mounted relative to the respective other part. In this case in particular it is advantageous if the at least one friction element is arranged on the form-fitting component.

Preferably, the at least one friction element is arranged on the pivot axis, preferably about the pivot axis. This allows for embodiments that are especially simple in terms of design. The at least one friction element is designed, for example, to be ring-shaped, wherein the pivot axis, which is designed as a shaft in this case, is guided through the preferably central opening of the ring-shaped friction element. Due to the rotational symmetry about the pivot axis, a uniform and constant frictional torque can be achieved, irrespective of the position and orientation and in particular of the pivot angle of the foot part relative to the lower leg part. Since the foot part and the lower leg part are preferably not locked relative to each other in the area of the pivot axis, a friction element arranged in this area causes no disruption when the locking is released and recreated at a different pivot angle.

In a preferred embodiment of the prosthetic foot, the pivot axis is a virtual pivot axis. Specifically, this means that there is no part of the prosthetic foot that acts as a shaft about which the foot part can be pivoted relative to the lower leg part. This allows the pivot axis to be moved well into the range of the prosthetic foot, altering and often improving foot motion patterns. To achieve this, the foot part and the lower leg part feature correspondingly designed form-fitting elements, for example. This may be a groove and a correspondingly shaped tongue, both of which are curved in the shape of a circular arc. Since the groove and the tongue have the same radius of curvature, the foot part can be pivoted relative to the lower leg part by displacing the tongue in the groove. The pivot axis, which in this case is a virtual pivot axis, extends through the center point of the circular arc.

Preferably, the at least one friction element features a coating of a bearing surface of the foot part and/or a bearing surface of the lower leg part and/or a bearing surface of a third component, such as a shaft or the form-fitting component. Alternatively or additionally, the at least one friction element has at least one damping element, especially a hydraulic damping element. In this case, the prosthetic foot comprises, for example, a volume filled with a fluid, in particular a hydraulic oil. This volume is preferably arranged on the foot part or the lower leg part and preferably completely filled with the fluid. A slide is arranged on the respective other component, i.e. the lower leg part or the foot part, such that it is torque-proof, said slide projecting into the fluid-filled volume. If the foot part is now pivoted relative to the lower leg part, the slide is moved in the volume. The fluid opposes this movement with a flow resistance that depends on the viscosity and the geometric conditions. This relates, for example, to the ratio of the cross-sectional area of the volume relative to the cross-sectional area of the slide in a direction perpendicular to the pivot direction. The greater the viscosity of the fluid and the more similar the cross-sectional area of the slide to that of the volume, the greater the resistance and therefore also the frictional torque.

Even if such a hydraulic damper does not generate mechanical friction in the sense of two solid bodies rubbing against each other, these hydraulic torques and forces are preferably also understood as frictional torques in the sense of the present invention.

The frictional element preferably has no impact on a clearance the axial direction between the lower leg part and the foot part.

In the following, a number of embodiment examples of the invention will be explained in more detail with the aid of the accompanying drawings. They show FIGS. 1 to 4—schematic sectional views through parts of prosthetic feet according to some embodiment examples of the present invention, FIGS. 5 and 6—schematic views of the ankle moments during a step cycle, FIGS. 7 and 8—schematic sectional views through parts of prosthetic feet according to further embodiment examples of the present invention, FIG. 9—the schematic view of a prosthetic foot according to an embodiment example of the present invention, FIG. 10—the schematic view of a further prosthetic foot, FIG. 11—the schematic view of two components of a prosthetic foot and FIGS. 12 and 13 schematic views of part of a prosthetic foot.

FIG. 1 shows a sectional view through a part of a prosthetic foot, wherein a foot part 2, of which only a fastening element is shown, is connected to a lower leg part 4 such that it can be pivoted about a pivot axis 6. Only a part of the lower leg part 4 with an adapter 8 is shown, to which a further prosthetic part can be fastened. In FIG. 1, the lower leg part 4 is connected with a shaft 10 in a torque-proof manner, the pivot axis 6 extending within said shaft and said shaft being rotatably mounted in two specially provided mounts 12 in the foot part 2. In FIG. 1, a friction element 14 is located between the lower leg part 4 and the right side of the foot part 2, said friction element being arranged about the shaft 10 in the embodiment example shown. A screw 16 is arranged in a specially provided thread bore in the shaft 10, said screw having a screw head 18. A disc spring 20 is located between the screw head 18 and the outside of the foot part 2, wherein said spring can be compressed and thus energetically charged by screwing the screw 16 into the shaft 6. The disc spring 20 supports itself on the outside of the foot part 2, so that the lower leg part 4 fixed on the shaft 10 is pulled by the screw 16 and the disc spring 20 towards the right leg of the element of the foot part 2 shown, thereby compressing the friction element 14. In this way, the frictional torque applied by the torque element 14 can be adjusted.

Here, the frictional torque applied by the friction element 14 counteracts a pivoting of the foot part 2 relative to the lower leg part 4. A clearance in the axial direction in relation to the pivot axis 6 between the foot part 2 and the lower leg part 4, which is represented by the gap 22, is not affected by the friction element 14 in the embodiment example shown. A locking element can lock the foot part 2 and the lower leg part 4 relative to each other along the drawn line 24; however, a clearance in the pivot direction about the pivot axis 6 remains.

FIG. 2 depicts a similar embodiment in which the lower leg part 4 is connected in a torque-proof manner to the shaft 10 in which the axis 6 extends. In contrast to the embodiment shown in FIG. 1, in FIG. 2 there are two friction elements 14 arranged between the two legs of the foot part 2. Instead of the screw 16 with the disc spring 20 arranged under the screw head 18, a wedge 26 is inserted into the shaft 10 on the right-hand side, said wedge expanding the shaft 10 at that point and thus enabling the force transmission required.

FIG. 3 shows a foot part 2 that is connected to the shaft 10 such that it is torque-proof. The lower leg part 4 is rotatably mounted on this shaft 10. A friction element 14 is located between the left leg of the foot part 2 and the lower leg part 4, while a disc spring 20 is located on the opposite side. Said spring is tensioned and compressed by the screw 16 passing through the shaft 10, thereby creating the necessary force.

FIG. 4 depicts a similar embodiment to FIG. 3 in which the foot part 2 is connected in a torque-proof manner to the shaft 10, on which the lower leg part 4 is mounted in a torque-proof manner. A friction element 14 is arranged on each side of the lower leg part 4, said friction elements being compressed by the force applied by the screw 16 and the disc spring 20.

FIG. 5 shows a schematic diagram that depicts the course of the ankle moment (y axis) over the step cycle (x axis). The cycle begins with the heel strike, from which point onwards a negative torque is exerted that acts on the ankle in the plantar flexion direction. Due to the clearance, the foot part and lower leg part strike against each other, which is depicted by the cloud 28. Over the course of the step, the torque initially increases in strength, which leads to it becoming more negative in FIG. 5. From the moment at which the foot is fully on the ground, a positive torque is exerted, which acts on the ankle in the dorsal flexion direction. At the transition, the torque changes sign and a zero crossing occurs, which is shown by the cloud 30. As the direction of the acting torque changes, another impact occurs between the foot part and the lower leg part, which is associated with a noise upon impact in prosthetic feet according to the prior art. In the present invention, this noise is reduced or even completely prevented by the frictional torque.

Only when the foot leaves the ground again (toe-off) does the torque return to zero and the third impact of the foot part and the lower leg part occurs, shown by the cloud 32.

Figure 6:
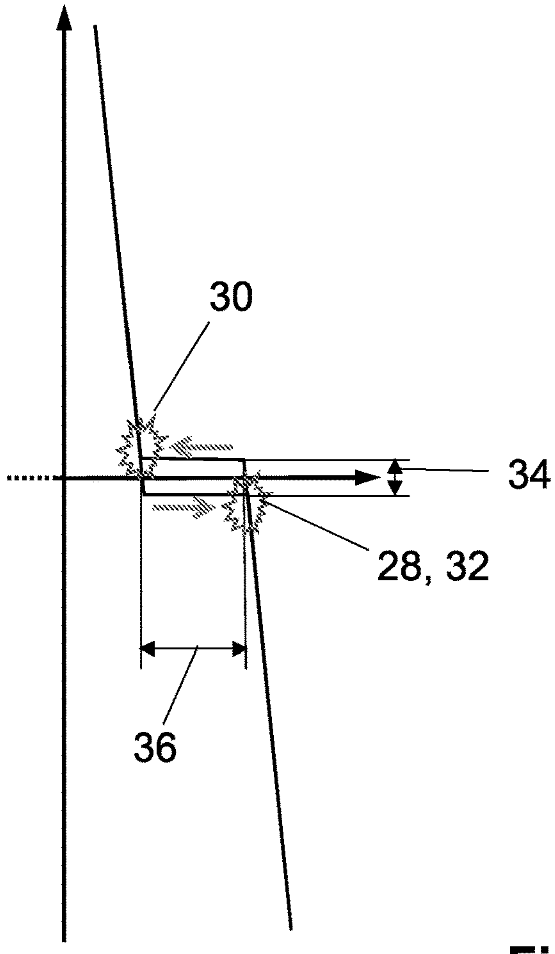

FIG. 6 depicts a schematic enlargement during the respective stops. In the case of the stops depicted by the clouds 28, 32, the curve of the torque extends from left to right, i.e. from the positive torque to the negative torque. Here, the acting torque must be slightly negative before the movement between the foot part and the lower leg part enabled by the clearance occurs. The distance 34 corresponds to twice the frictional torque. If the movement occurs, the angle between the foot part and the lower leg part slides to the right by an amount, which is depicted by the distance 36. This distance corresponds to the clearance. In the case of the impact indicated by the cloud 30, the torque is reversed.

Figure 7:
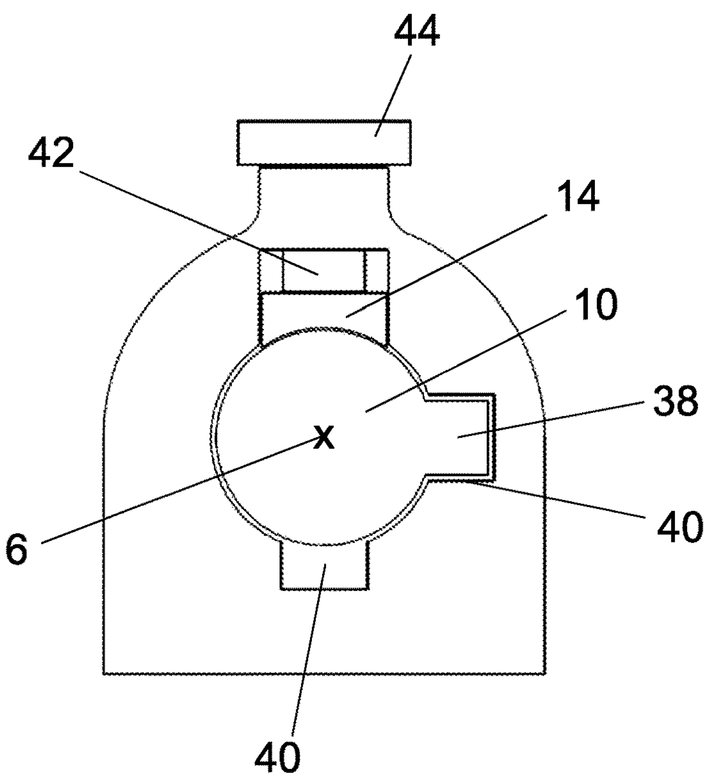

FIG. 7 shows a sectional view through a part of a prosthetic foot perpendicular to the pivot axis 6. The latter features a projection 38 which can be inserted into 2 specially provided recesses 40. A friction element 14 is arranged in such a way that it comes into contact with the shaft 10, thereby applying a frictional torque. A pressure exerted by the friction element 14 on the shaft 10 can be adjusted via a screw 42 that is connected to an actuation element 44. As such, the frictional torque can also be adjusted.

Figure 8:
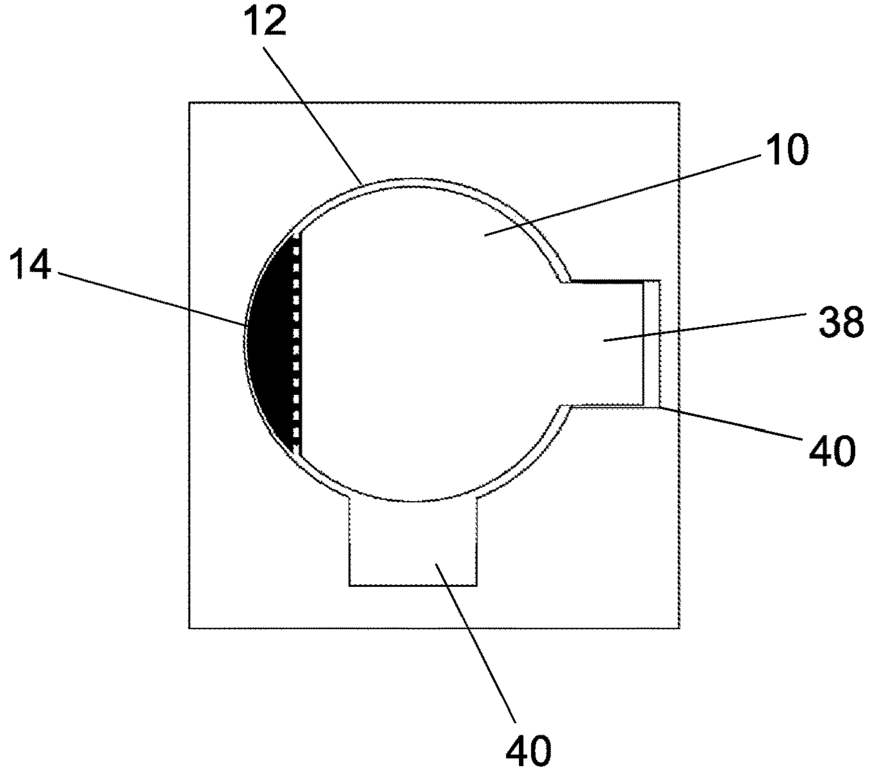

FIG. 8 depicts a similar view. The shaft 10 features the projection 38, which can be engaged in the recesses 40. A friction element 14 is shown on the side of the shaft 10 opposite the projection 38, said friction element exerting a frictional torque on the inside of the mount 12 in which the shaft 10 is mounted.

Figure 9:
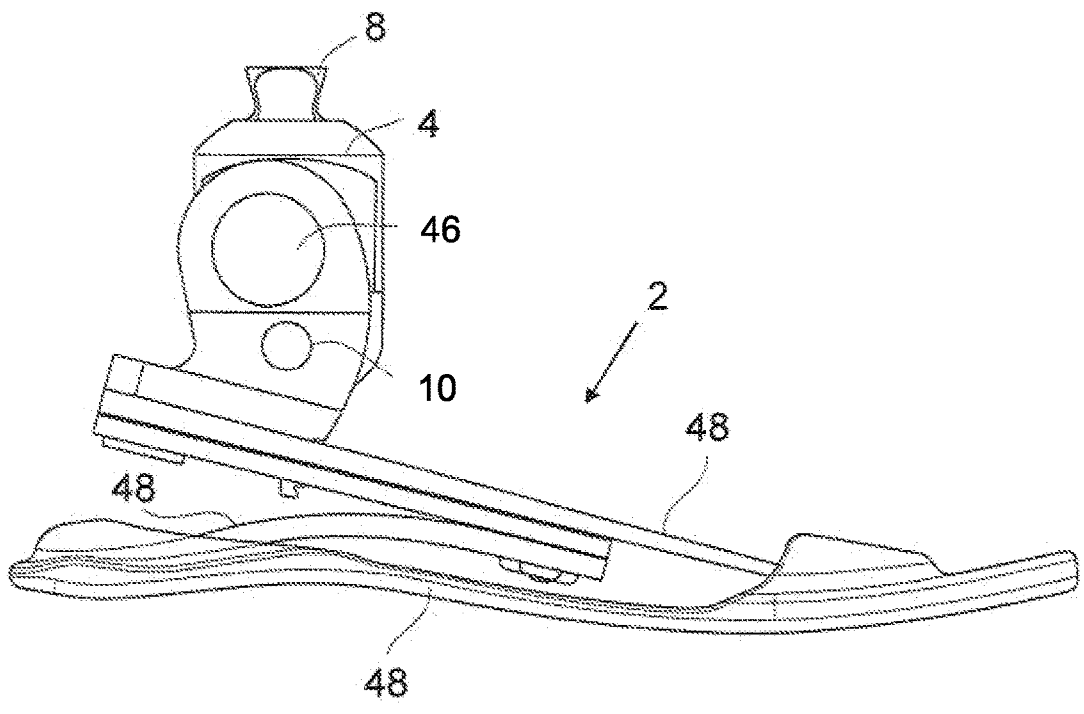

FIG. 9 shows a prosthetic foot with the foot part 2 and the lower leg part 4 on which an adapter 8 is located. The foot part 2 can be pivoted relative to the lower leg part 4 via the shaft 10. A form-fitting element 46, which is not shown in FIG. 9 and is connected to the lower leg part 4, for example in a torque-proof manner, can be displaced along a displacement direction, for example by actuating an actuation element, for example by pressing a button, said direction being perpendicular on the drawing plane in the embodiment shown in FIG. 9. In the engaged state, the form-fitting element engages in a correspondingly designed second form-fitting element that is fixed to the foot part in a torque-proof manner. Due to the clearance between the lower leg part 4 and the foot part 2 and the respective form-fitting elements, a small movement is still possible. The foot part 2 also features various springs 48, which ensure the required elasticity. The friction element 14 is not visible in the view shown. Preferably, the form-fitting element to be disengaged is spring-loaded in the direction of the engaged position.

Figure 10:
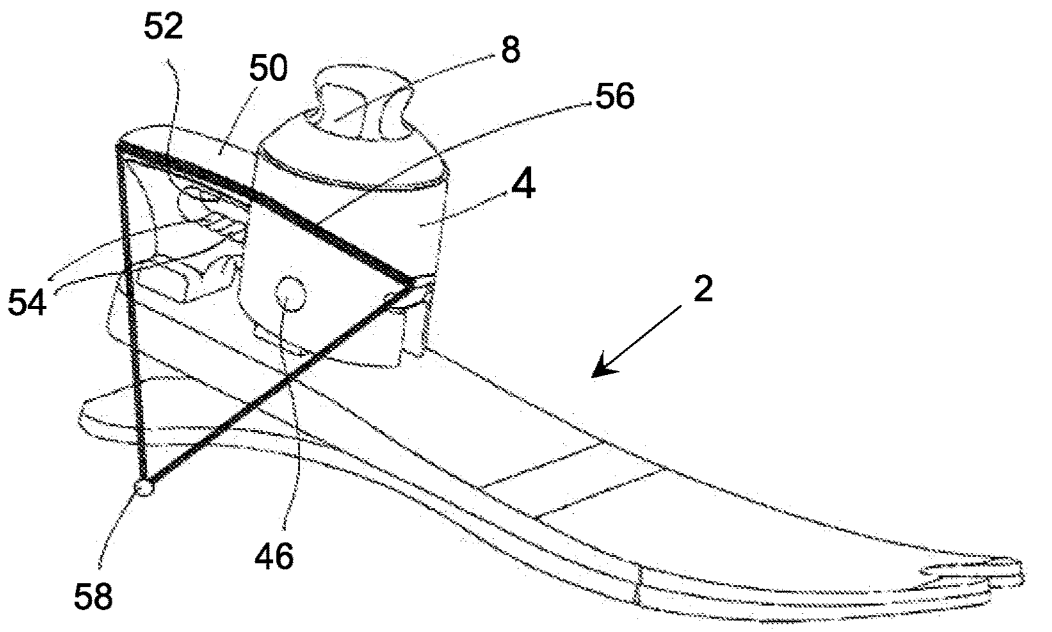

FIG. 10 shows a further embodiment of a prosthetic foot with the foot part 2 and the lower leg part 4 on which an adapter 8 is located. A rail 50 is located on the foot part 2 that the lower leg part 4 can glide along. It has an elongated hole 52 with multiple grooves 54 that serve as different locking position for the lower leg part 4 on the rail 50. The form-fitting element 46, which in this case is designed as a pin, for example, can be fixed in each of these grooves 54, thereby locking the lower leg part 4 in the respective position. To this end, the pin 46 can be disengaged, for example, manually or mechatronically and thus disengaged from the grooves 54. The position of the lower leg part 4 can then be displaced and adjusted relative to the foot part 2. The pin 46 is then re-engaged and thus re-engaged with one of the grooves 54. In the embodiment example shown, the lower leg part 4 can consequently displaced along the line 56, which is designed in the shape of a circular arc and features a virtual point of rotation 58.

Figure 11:
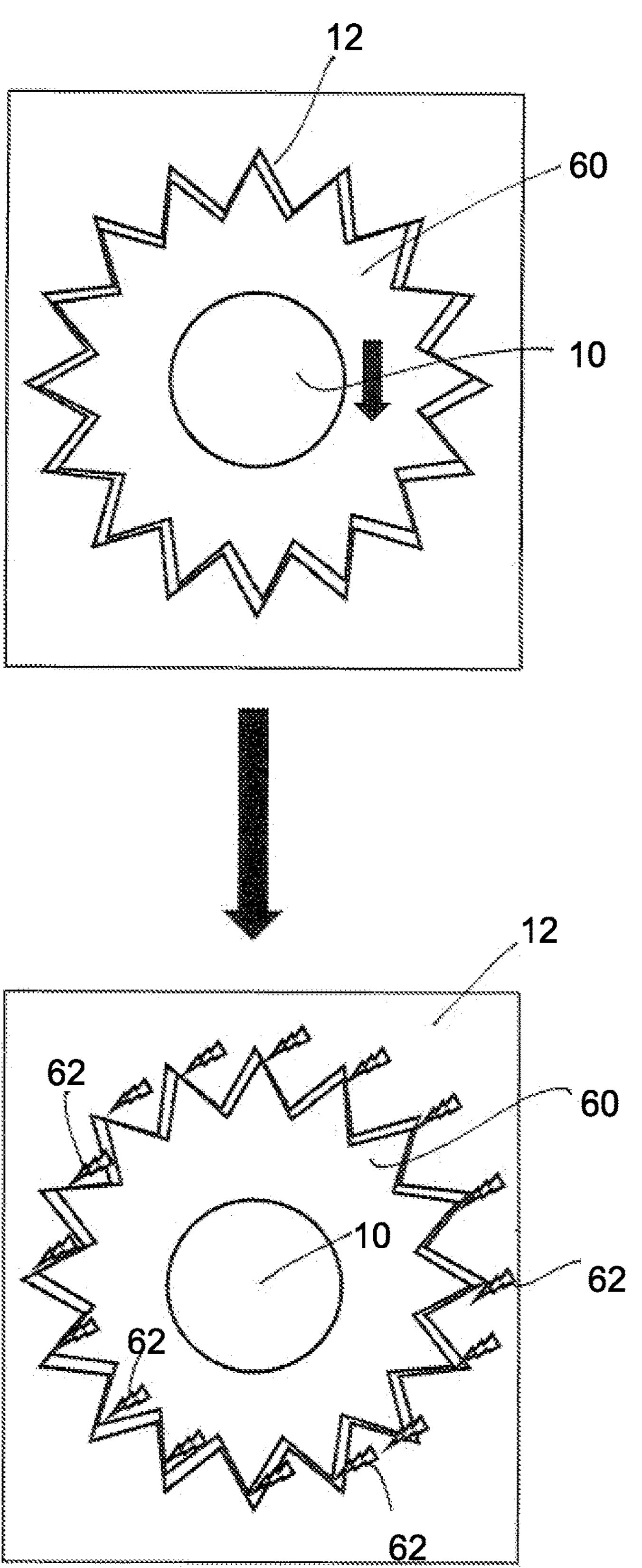

FIG. 11 schematically depicts how the problem to be solved by the present invention emerges. Schematically visible is a gearwheel 60 which is connected to the shaft 10 in a torque-proof manner in the embodiment example shown. The combination of gearwheel 60 and shaft 10 is arranged in a mount 12, which is designed as a hollow gearwheel. The mount is connected to the lower leg part 4 or the foot part 2 and the gearwheel 60 with the respective other part.

In the upper part of FIG. 11, the gearwheel 60 subjected to a counter-clockwise torque with the shaft 10, so that the respective counter-clockwise flanks of the individual teeth of the gearwheel 60 rest on the respective flanks of the inwardly projecting teeth of the mount 12. Upon the transition to the lower part of FIG. 11, the load direction changes and the torque acting on the shaft 10 changes sign. Under this torque, the gearwheel 60 is loaded clockwise with the shaft 10. Due to the clearance between the gearwheel 60 and the mount 12, a minimal movement of the two components relative to each other is possible until the situation depicted in the lower part of FIG. 11 is reached. In this situation, the counter-clockwise flanks of the teeth of the gearwheel 60 rest on the inwardly projecting teeth of the mount 12. As a minimal movement has taken place between the upper situation in FIG. 11 and the lower situation, a noise occurs at each point where a tooth of the gearwheel 60 strikes the mount 12, said noise being indicated by the arrows 62.

Figure 12:
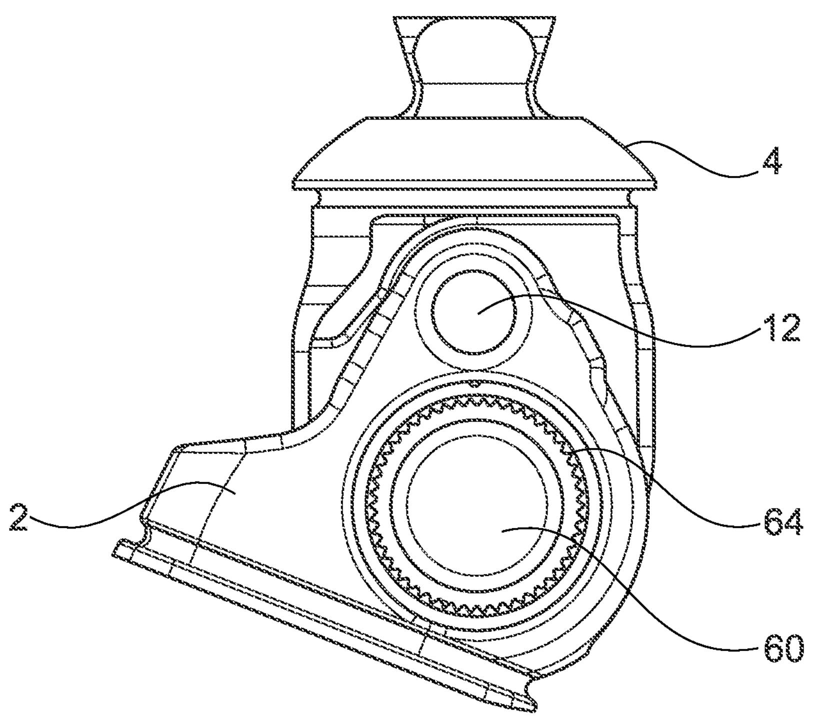
Figure 13:
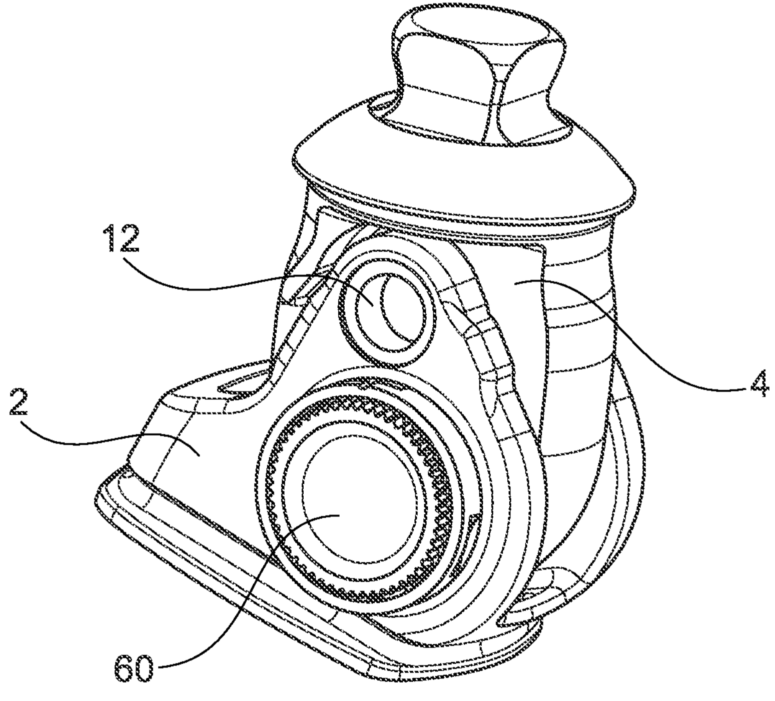

FIGS. 12 to 13 show two views of a joint of a prosthetic foot according to an embodiment example of the present invention. One can see part of the lower leg element 4 and of the foot part 2, which are arranged to pivot against each other about a pivot axis. They are arranged on a shaft 10, not depicted here, which is inserted into the mount 12 shown in FIG. 12. In FIG. 12, the gearwheel 60 is shown in the engaged state. It engages in a correspondingly designed form-fitting element 64 which, like in FIG. 11, is designed as a mount. It results in the situation depicted in FIG. 11.

FIG. 13, on the other hand, shows the gearwheel 60 in the disengaged position. It has been displaced along a displacement direction, which in FIG. 13 extends parallel to the mount 12 through which the shaft can be pushed, and thus disengaged from the correspondingly designed form-fitting element 64.

REFERENCE LIST

2 foot part
4 lower leg part
6 pivot axis
8 adapter
10 shaft
12 mount
14 friction element
16 screw
18 screw head
20 disc spring

22 gap
24 line
26 wedge
28 cloud
30 cloud
32 cloud
34 distance
36 distance
38 projection
40 recess
42 screw
44 actuation element
46 form-fitting element
48 spring
50 rail
52 elongated hole
54 groove
56 line
58 virtual point of rotation
60 gearwheel
62 arrow
64 corresponding form-fitting element

The invention claimed is:

1. A prosthetic foot, comprising:

a foot part;

a lower leg part;

a connection between the lower leg part and that the foot part, wherein the lower leg part is connected to the foot part such that it can be pivoted about a pivot axis, and wherein the lower leg part is lockable in various pivot angles relative to the foot part, wherein the connection between the lower leg part and the foot part has a clearance between the foot part and the lower leg part when the foot part is locked on the lower leg part; and at least one friction element arranged on and about the pivot axis between the foot part and the lower leg part which applies a frictional torque that counteracts a pivoting of the foot part relative to the lower leg part when the foot part is locked relative to the lower leg part, wherein the lower leg part is lockable relative to the foot part by a form-fitting connection, wherein the lower leg part and the foot part each comprise form-fitting elements designed to correspond to each other, and wherein the at least one friction element is arranged on at least one of the form-fitting elements.

2. The prosthetic foot according to claim 1, wherein the at least one friction element is configured to generate the frictional torque independently of whether the foot part is locked relative to the lower leg part, so that the lower leg part also has to be pivoted relative to the foot part against the frictional torque.

3. The prosthetic foot according to claim 1 wherein the at least one friction element comprises a coating of a bearing surface of the foot part and/or a bearing surface of the lower leg part and/or a bearing surface of a third component.

4. The prosthetic foot according to claim 1 wherein the at least one friction element has no impact on a clearance in an axial direction between the lower leg part and the foot part.

5. The prosthetic foot according to claim 1 wherein the at least one friction element comprises a damping element.

6. The prosthetic foot according to claim 1 wherein the at least one friction element comprises a coating of bearing surface of a third component, wherein the third component is selected from the group of a shaft and a form fitting component.

7. The prosthetic foot according to claim 5 wherein the damping element is a hydraulic damping element.

8. A prosthetic foot, comprising:

a foot part;

a lower leg part;

a connection between the lower leg part and that the foot part, wherein the lower leg part is connected to the foot part such that it can be pivoted about a pivot axis, and wherein the lower leg part is lockable in various pivot angles relative to the foot part, wherein the connection between the lower leg part and the foot part has a clearance between the foot part and the lower leg part when the foot part is locked on the lower leg part; and at least one friction element arranged on and about the pivot axis between the foot part and the lower leg part which applies a frictional torque that counteracts a pivoting of the foot part relative to the lower leg part when the foot part is locked relative to the lower leg part, wherein the lower leg part is lockable relative to the foot part by a form-fitting connection, and wherein the lower leg part and the foot part each comprise form-fitting elements that are designed to correspond to a separate form-fitting component, wherein the at least one friction element is arranged on the form-fitting component and/or on at least one of the form-fitting elements.

9. The prosthetic foot according to claim 8, wherein the form-fitting component is mountably mounted on the lower leg part or the foot part.

* * * * *